United States Patent
Devereaux et al.

(10) Patent No.: US 8,736,517 B2
(45) Date of Patent: May 27, 2014

(54) WIRELESS AUGMENTED REALITY COMMUNICATION SYSTEM

(71) Applicant: Innovation Management Sciences, Mountain View, CA (US)

(72) Inventors: Ann Devereaux, Tujunga, CA (US); Thomas Jedrey, Pasadena, CA (US); Martin Agan, Mountain View, CA (US)

(73) Assignee: Innovation Management Sciences, Mountain View, CA (US)

( * ) Notice: Subject to any disclaimer, the term of this patent is extended or adjusted under 35 U.S.C. 154(b) by 0 days.

(21) Appl. No.: 14/038,760

(22) Filed: Sep. 27, 2013

(65) Prior Publication Data

US 2014/0091948 A1    Apr. 3, 2014

Related U.S. Application Data

(63) Continuation of application No. 13/723,472, filed on Dec. 21, 2012, now Pat. No. 8,633,869, which is a continuation of application No. 12/698,107, filed on Feb. 1, 2010, now abandoned, which is a continuation of application No. 11/410,517, filed on Apr. 24, 2006, now abandoned, which is a continuation of application No. 09/483,315, filed on Jan. 14, 2000, now Pat. No. 7,035,897.

(60) Provisional application No. 60/115,993, filed on Jan. 15, 1999.

(51) Int. Cl.
*G09G 5/00* (2006.01)

(52) U.S. Cl.
USPC ............................................. 345/7; 345/156

(58) Field of Classification Search
USPC ......... 345/7, 156; 455/550, 566; 348/14, 211, 348/223
See application file for complete search history.

(56) References Cited

U.S. PATENT DOCUMENTS

| | | | |
|---|---|---|---|
| 4,258,387 A | 3/1981 | Lemelson et al. |
| 5,202,756 A | 4/1993 | Sasaki et al. |
| 5,305,244 A | 4/1994 | Newman et al. |
| 5,386,233 A | 1/1995 | Keith |
| 5,402,414 A | 3/1995 | Asai |
| 5,495,576 A | 2/1996 | Ritchey |
| 5,550,754 A | 8/1996 | McNelley et al. |
| 5,557,320 A | 9/1996 | Krebs |
| 5,570,367 A | 10/1996 | Ayanoglu et al. |
| 5,579,375 A | 11/1996 | Ginter |
| 5,664,006 A | 9/1997 | Monte et al. |
| 5,689,300 A | 11/1997 | Shibata et al. |
| 5,710,798 A | 1/1998 | Campana, Jr. |
| 5,749,052 A | 5/1998 | Hidem et al. |
| 5,759,044 A | 6/1998 | Redmond |

(Continued)

*Primary Examiner* — Ricardo L Osorio

(57) ABSTRACT

The system of the present invention is a highly integrated radio communication system with a multimedia co-processor which allows true two-way multimedia (video, audio, data) access as well as real-time biomedical monitoring in a pager-sized portable access unit. The system is integrated in a network structure including one or more general purpose nodes for providing a wireless-to-wired interface. The network architecture allows video, audio and data (including biomedical data) streams to be connected directly to external users and devices. The portable access units may also be mated to various non-personal devices such as cameras or environmental sensors for providing a method for setting up wireless sensor nets from which reported data may be accessed through the portable access unit. The reported data may alternatively be automatically logged at a remote computer for access and viewing through a portable access unit, including the user's own.

14 Claims, 3 Drawing Sheets

(56) References Cited

U.S. PATENT DOCUMENTS

| | | |
|---|---|---|
| 5,809,176 A | 9/1998 | Yajima |
| 5,815,080 A | 9/1998 | Taguchi |
| 5,844,601 A | 12/1998 | McPheely et al. |
| 5,844,824 A | 12/1998 | Newman et al. |
| 5,850,352 A | 12/1998 | Moezzi et al. |
| 5,864,681 A | 1/1999 | Proctor et al. |
| 5,926,624 A | 7/1999 | Katz et al. |
| 6,026,082 A | 2/2000 | Astrin |
| 6,035,349 A | 3/2000 | Ha et al. |
| 6,044,088 A | 3/2000 | Rahman et al. |
| 6,050,940 A | 4/2000 | Braun et al. |
| 6,058,104 A | 5/2000 | Snelling et al. |
| 6,105,060 A | 8/2000 | Rothblatt |
| 6,141,032 A | 10/2000 | Priest |
| 6,192,257 B1 | 2/2001 | Ray |
| 6,236,854 B1 | 5/2001 | Bradshaw, Jr. |
| 6,253,061 B1 | 6/2001 | Helferich |
| 6,285,757 B1 | 9/2001 | Carroll et al. |
| 6,295,302 B1 | 9/2001 | Hellwig et al. |
| 6,297,852 B1 | 10/2001 | Laksono et al. |
| 6,298,370 B1 | 10/2001 | Tang et al. |
| 6,314,302 B1 | 11/2001 | Haferbeck et al. |
| 6,317,039 B1 | 11/2001 | Thomason |
| 6,327,570 B1 | 12/2001 | Stevens |
| 6,356,945 B1 | 3/2002 | Shaw et al. |
| 6,384,846 B1 | 5/2002 | Hiroi |
| 6,385,593 B2 | 5/2002 | Linberg |
| 6,392,692 B1 | 5/2002 | Monroe |
| 6,404,928 B1 | 6/2002 | Shaw et al. |
| 6,438,384 B1 | 8/2002 | Chen |
| 6,487,663 B1 | 11/2002 | Jaisimha et al. |
| 6,522,352 B1 | 2/2003 | Strandwitz et al. |
| 6,526,538 B1 | 2/2003 | Hewitt |
| 6,600,734 B1 | 7/2003 | Gernert et al. |
| 6,810,035 B1 | 10/2004 | Knuutila et al. |

WIRELESS AUGMENTED REALITY COMMUNICATION SYSTEM

RELATED APPLICATIONS

This application is a continuation of U.S. patent application Ser. No. 13/723,472 filed Dec. 21, 2012, which is a continuation of U.S. patent application Ser. No. 12/698,107 filed on Feb. 1, 2010, which is a continuation of U.S. patent application Ser. No. 11/410,517 filed on Apr. 24, 2006, now abandoned, which is a continuation of U.S. patent application Ser. No. 09/483,315 filed on Jan. 14, 2000, now issued U.S. Pat. No. 7,035,897, which claims priority from U.S. Provisional Application No. 60/115,993 filed on Jan. 15, 1999.

GOVERNMENT LICENSE RIGHTS

The U.S. Government has certain rights in this invention pursuant to NAS7-1407 awarded by NASA.

BACKGROUND OF THE INVENTION

1. Field of the Invention

The invention is a wireless augmented reality system (WARS) that leverages communications and multimedia information processing microelectronics, along with displays, imaging sensors, biosensors, and voice recognition to provide hands-free, tetherless, real-time access and display of network resources, including video, audio and data.

2. Description of the Prior Art and Related Information

Online instruction manuals are becoming more prevalent in the industrial and everyday environment. These electronic technical manuals (ETM) may be interactive. Just as with printed manuals, ETMs may become very difficult to use and maintain in these environments where elements of an environment, such as dust, chemical or general harshness may be detrimental to the electronics and storage devices used to display and operate the ETM. Further, it is not always possible for a worker who requires access to an ETM to stop work to consult ETM.

These problems are multiplied in extraterrestrial environments such as a space shuttle or a space station. During intra and extra vehicular activities, it may be virtually impossible to access a traditional keyboard and computer display to access an ETM. For example, during a satellite repair mission, it would not be practical for an astronaut in a bulky extravehicular space suit to type commands on a keyboard to view a display in the extreme environment of outer space where the sun glare may make viewing impossible.

Hands-free portable computers have been implemented in an attempt to solve some of these problems. For example, U.S. Pat. Nos. 5,305,244 and 5,844,824 describe systems in which a head-up display and voice recognition is implemented in a portable computer for displaying ETM. However, these systems, being a single user-to-computer paradigm, do not allow multiple-user access to multiple computers, multimedia devices or nodes on a network for accessing arbitrarily-selected data channels. Further, these previously-described systems are self contained and their data storage needs to be updated periodically to be sure that the latest data is displayed. Further, these systems do not allow two-way communication over local and wide area networks to other multimedia users and devices, and do not provide real-time biomedical information about the physical condition of the user.

There is thus a need for a wireless, wearable communications system allowing two-way voice, video and data communication between local users and to remote users and devices over network nodes, along with tetherless real-time monitoring of the local user's physical condition.

SUMMARY OF THE INVENTION

The system solves the above problems with prior art systems with an adaptive wireless remote access network comprised of small individual portable access units linked to a local cellular general purpose node. Interlinked general purpose nodes support communications across different habitat modules or internal-to-extravehicular communications, in the case of the space environment; terrestrial wired networks such as the Internet can serve as the interconnection of remotely scattered access nodes in an industrial, commercial or home environment application.

The system may provide shuttle and international space station astronauts with tetherless, on-demand access to data channels from multimedia devices such as cameras or audio sensors associated with other persons or in a stand-alone configuration, and multimedia or data display from a networked computer terminal and to the equipment control capabilities which may be available through that computer. Transparent to such access, the system can maintain a data channel for monitoring an astronaut's health or environment via in-situ sensors. Though this system may be used for the shuttle and the international space station, the system has uses in many possible applications related to medical, industrial, and commercial areas.

The invention is a personal communications system designed especially for the space shuttle or station environment to provide cellular communications access throughout the vessel with video, audio, data and computer connect services. A small, wearable portable access unit (PAU) communicates over high-rate link to a centrally-located network access unit, called a general purpose node herein. The system backbone provides 2-way video, 2-way audio, and a multi-purpose data channel between the PAU and general purpose node. One embodiment of the PAU used for personal communication has an attached headset with video display, audio feed and camera, which together may be used for audio or video teleconferencing. When used as a virtual terminal to a computer in the network, the user is able to view and manipulate imagery, text or video, using voice commands to control the terminal operations.

Using the system, an astronaut may efficiently operate and monitor computer-controllable activities inside or outside the vehicle or station. Hands-free access to computer-based instruction texts, diagrams and checklists replaces juggling manuals and clipboards, and tetherless computer system access allows free motion throughout a cabin while monitoring and operating equipment. Along with voice commands, an integrated "touchpad" on the PAU may be used for remote computer control through a sensor data channel; this return data channel may also be used for other control data as from a three-D mouse or data glove input device, allowing the real-time video display to be used for remote, wireless monitor and control of robotic cameras or manipulators.

Concurrent with information provided to the astronaut, the system also allows external observation of the astronaut's situation; personal biological or other sensors can send back continuous telemetry through personal access unit and general purpose node. A miniature camera integrated into the headset provides real-time video of the wearer's field of view to remote observers. In this way, for example, a principal investigator located on Earth may consult with a payload specialist on the operation or troubleshooting of their equipment.

The system provides wireless high-rate data exchange. The radio link is adapted to operate within a high-interference, high-multipath environment of a space shuttle or space station module. Radio frequency (RF) links do not require visual line-of-sight to operate, but the metal walls and lack of RF absorbers, combined with moving human bodies, creates an enormous potential for destructive self-interference of the radio signals. The integrated radio and multimedia data processing technology provides for efficient and high-quality video and audio data compression for noisy indoor communications channels. The system supports multiple-user access for video, audio, and sensor data services in the wireless coverage area. Potential applications of the system are in any environment where heads-up, hands-free information retrieval or multimedia communications access improves efficiency including tetherless operations/monitor consoles, remote consultations in medical or maintenance procedures, and hazardous/confined space activities. There are also in-the-home entertainment/communications applications.

Similar to the space extravehicular activities applications, bio-isolation suits have similar operation constraints to space suits. They are worn commonly where there are chemical or biological contaminates, and any extraneous materials brought into a chamber, such as clipboards or documents, also present a contamination risk. A unit suitably modified for use in a space suit could be used in this situation. This allows the user to use a computer (log data, use a check list, etc.), to communicate with colleagues, including providing first-hand video of work in progress, and to maintain constant monitoring of the health of the user.

An extension of the medical applications areas would be in remote telemedicine. Many medical diagnostic and treatment tools are being made portable and rugged enough to be taken to remote sites. Some examples are an ultrasound unit that is the size of a backpack, an entire intensive care unit of equipment built into a stretcher, and a trauma pod built into a cruise missile. For many of these devices, CRT or LCD panels comprise a significant amount of the bulk and weight of the devices. The system of the present invention may provide a replacement for the CRT or LCD panel as well as an interface to the control system of the device, while providing communications access through an interface to the remote site's existing communications equipment.

Industrial applications include use by inspection or maintenance crews in remote or dangerous environments such as oil refineries, drilling rigs, power plants, etc., where the personnel can move around with their hands and peripheral vision free to attend to their own safety and tasks. They would be in constant contact with the information they needed and any technical assist could be given by individuals looking at the return video images from the user.

An example of a commercial application is for mission control and other operations personnel who presently must sit at a display console for hours at a time. These individuals could make use of the system of the present invention to increase their mobility and efficiency.

DETAILED DESCRIPTION OF PREFERRED EMBODIMENTS

Figure 1:
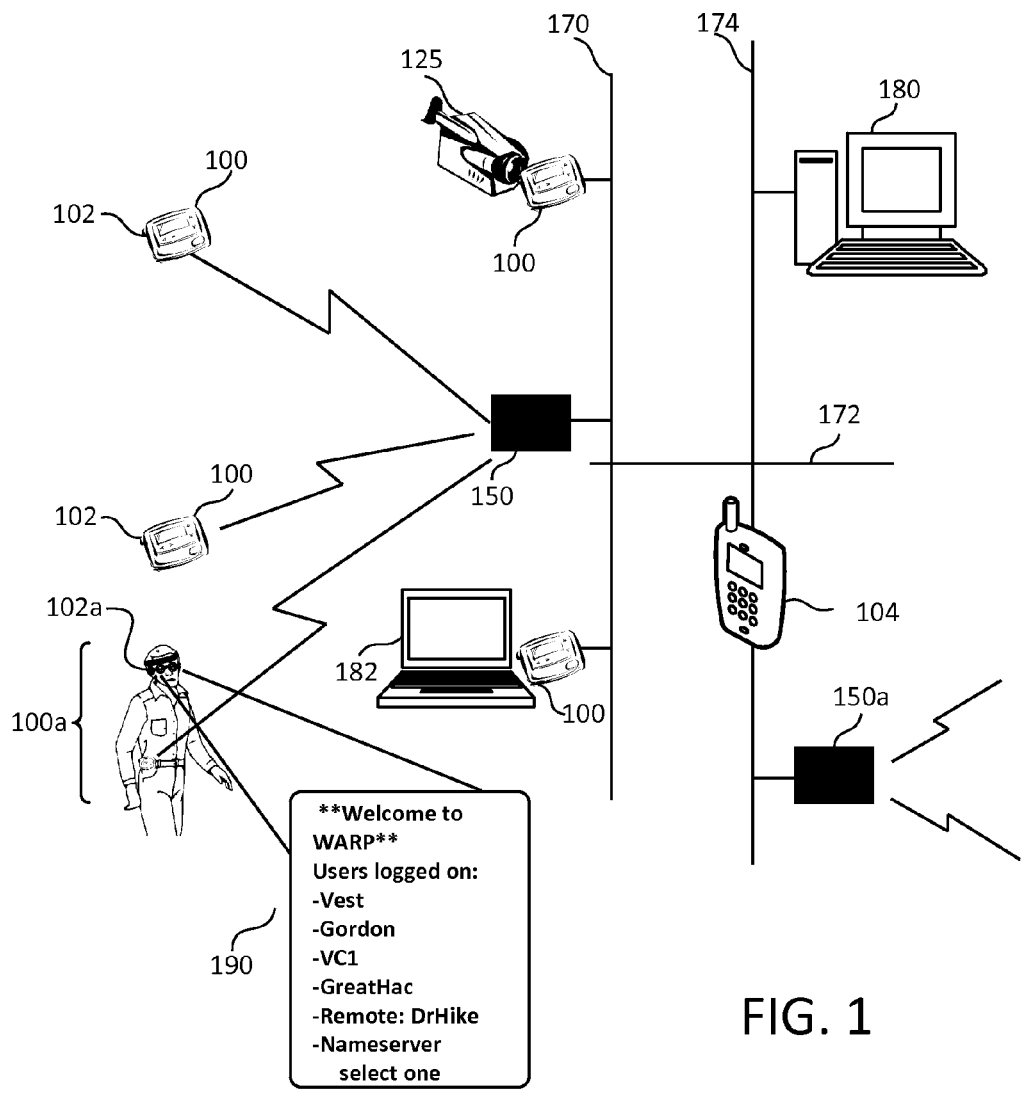
FIG. 1 is a diagrammatic illustration of the components of the system of the present invention.

With reference to FIG. 1, a diagram illustrating components of the system of the present invention is shown. The system may comprise small pager-like devices called portable access units 100. The portable access units 100 are accessorizable for different "multimedia" interfaces for display, camera, audio and sensor operation. Another embodiment of the portable access unit 100a comprises a wearable headset and microphone assembly 102a.

The portable access units 100-100a interface directly through wireless link with a network through a general purpose node 150. The general purpose node 150 allows wireless-to-wire communication with a local network 170. The local area network 170 may be electrically connected to a wide area network or Internet 172 in order to connect to remote local area networks 174. Alternatively, the general purpose node 150 may be directly connected to the wide area network 172. The general purpose node 150 may thus act as a router for routing video, display, audio and control data packets between the portable access units 100 and other, or remote, portable access units 100 or remote media devices 125, 180, etc connected to the networks 170-174. The connection with a network 170-174 may occur directly in electrical connection with one of the networks 170-174, or in wireless communication through a remote general purpose node 150a that is electrically connected to the network. The portable access units 100 may provide communication to and from remote media devices comprising computers 180-182 running specialized client software or certain commercial multimedia Internet software products such as video conferencing products that adhere to the industry standard H.323 for multimedia data transfer.

Each portable access unit 100-100a may dynamically associate with the closest general purpose node 150-150a when it is logged on to the network 170-174 or is connected thereto. Each general purpose node 150-150a records the associations and registers each portable access unit 100-100a on a list of connections associated with the particular general purpose node 150-150a. The list of connections is stored in a random access memory device included in the general purpose node 150-150a. When a portable access unit 100 is logged off or disconnected from the network 170-174, it is disassociated from the particular general purpose node 150-150a that it was associated with, and thus, is removed from the list of connections.

As shown on an example selection list screen 190 that may be presented on a display 102 or headset 102a on any of the portable access units 100-100a, the user can set up a video, audio, or data link with any other portable access unit 100-100a or remote media device 125, 180, etc, that is logged onto a network 170-174. The headset 102a may comprise a heads-up display (120 in FIG. 2) inside a headset embodying a transparent color LCD device. Using control keys or voice commands, a user of the portable access unit 100-100a may select a local or remote portable access unit 100-100a on a selection list 190 of other portable access units 100-100a or media devices 125, 180. The selection list 190 comprises a combination of the lists of connections stored on all of the general purpose nodes 150-150a. Users may further access a nameserver located on the access node 150 for locating remote unfamiliar portable access units 100-100a or remote media devices.

By selecting entries from the selection list 190, users may communicate with portable access units 100-100a or various media devices such as cameras 125, internet phones 104, one or more computers 180-182 located throughout the networks 170-174. A user may further select from the list 190 user names representing users of other portable access units 100 that are logged in and associated with remote general purpose nodes 150a connected to the networks 170-174.

Figure 2:
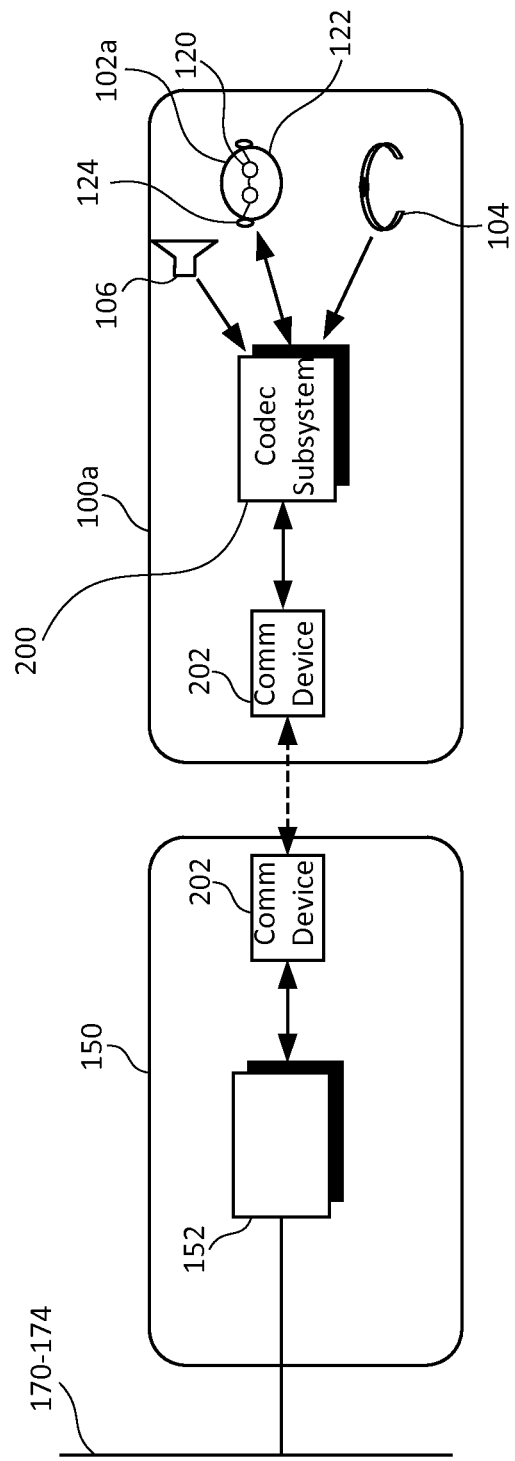
FIG. 2 is block diagram illustrating communications components used by the personal access unit and general purpose node of the system of FIG. 1.

With reference to FIG. 2, the components of the access node 150 and the wearable headset embodiment of the portable access unit 100a is shown. Elements for both the general purpose access node and portable access unit 100a include a communications device 202. Data processing functions are implemented in the form of an audio/video coder/decoder (codec) pair 200, one codec 200 comprising part of the portable access unit 100a and the other codec 200 being part of another portable access node 100a or remote media device for which it is desired to exchange signals. At a portable access node, the codec 200 controls a digital data stream which is fed to the communications device 202, which is implemented as an RF modem transceiver pair with an equivalent communications device 202 located in the general purpose access node. The codecs 200 serve as the interfaces to the external elements (including possibly the user display 102a and the sensor 104) on both sides of the communication continuum comprising the communications device 202 of the general purpose node 150, an internal network interface protocol circuit 152, the external networks 170-174 and the electrical connection or general purpose access node connection to the desired remote portable access node or media device. The internal network interface protocol circuit 152 may comprise an Ethernet chip, memory and a network protocol chip. With this architecture, the system addresses the issues of multiple-access and data channel quality, through the implementation of the communications device 202. Multiple implementations of the communication device 202 in the general purpose node 150 allows for multiple simultaneous communication links with a plurality of portable access units 100-100a for the general purpose node 150.

With the base functionality of the communications device 202 and codec subsystem 200, the architecture provides flexibility in utilization of different external components such as different headset 102a configurations, sensor 104 packages, and network interface 152 capabilities.

The communication device 202 is designed to operate in a high multipath space station or terrestrial indoor environment while being able to support multiple users at high, multimedia-type bandwidths. Thus the communications device's 202 physical (PHY) and media access (MAC) layers in combination support multiple access, dynamic network association, channel error rates of broadcast video quality (1×10e-6), and data rates up to broadcast-quality video bandwidths (on the order of 768 kbps per user (one-way)). Modulation to achieve this performance will be differential phase-shift keying, of binary or higher order (quadrature or high-order quadrature amplitude modulation); the order chosen reflects the necessary user data volume to be supported within fixed, FCC-specified bandwidth allocations. Orthogonal frequency division multiplexing, code division multiple access, and frequency hopping/time division multiple access may be used for achieving multiple access. Spread spectrum, channel equalization, antenna diversity and retransmission techniques may also be used for improving the reliability of the communications link. Through a combination of these technologies, two-way multimedia channel throughputs can be achieved for each of multiple simultaneous users. A variety of RF frequencies may be used, but the determining factor in frequency band selection is the availability in the band of a relatively large amount of spectrum in the space station or FCC terrestrial allocations, allowing the transmission of compressed video. Ranges in the 2.5 to 5.7 band range are preferable due to the FCC bandwidth available, the compactness of RF elements required at these frequencies, and the potentially low amount of interference that will be sustained. The RF front end of both the portable access unit 100-100a and general purpose node 150-150a may be interchangeable with different frequency front ends for system use in different frequency bands.

Low-rate, single user implementations of the communications system may be effected through adapted commercial wireless-LAN type products following the FCC 802.11 standard such as a frequency-hopping 2.4 GHz wireless LAN transceiver by Waveaccess, Inc of Wellesley, Mass., or direct-sequence spread-spectrum 2.4 GHz wireless LAN chipset by Harris Prism of Melbourne, Fla. These radio implementations, as with commercial implementations of the industry-proposed Bluetooth and HomeRF standards, will be limited in user access and overall throughput, however, and therefore unsuitable to real-time video teleconferencing for multiple users. The preferred embodiment for full capability is to implement the communications devices' physical and media access control layers in custom ASIC circuits allowing for support of all system capabilities within microelectronics architecture for small size and low power draw, providing pager-type form factor of wearable personal access units 100-100a.

The communications device 202 comprises a buffer memory and a radio frequency front end. Data modulation/demodulation circuits and error detection/correction protocol circuits are further included. Various combinations of these circuits may be obtained from Proxim of Sunnyvale, Calif., Harris of Melbourne, Fla. and Stanford Telecom of Stanford, Calif. Alternatively, all of the various circuitry may be implemented with an application specific integrated circuit (ASIC), or a combination of an ASIC and discrete elements for size and weight efficiency.

Three classes of headsets 102a may be used: hi-resolution military systems which are CRT based and may be provided by Honeywell of Morristown, N.J., or Hughes Network Systems of San Diego, Calif.; medium resolution industrial systems which are CRT or LED based scanners and may be provided by Intervision of Santa Clara, Calif.; or low to medium resolution entertainment systems which are color viewfinder LCD based systems that may be supplied by Virtual Vision of Redmond, Wash. (the V-CAP and E-GLASS), Sony Europe of Hampshire, United Kingdom (GLASSTRON VISOR) or Olympus of San Jose, Calif. Typical headset display 120 specifications for the portable access unit 100a include the following:

- RESOLUTION: Comparable at least to VGA (640×480) or better to 1280×1024 w/off-the-shelf display & I/O configuration
- DISPLAY: >10 FL/day, Display Bright.Ratio:>2, Brightness range:2 $OOM_{max}$
- FOV: 40-60 deg, Gray scale: >12
- EyeRelief: 20-26 mm TSP, 14/10 mm (on/off-axis) exit pupil
- Unif: 2:1 across 2/3 FOV, GLARE:<2.5% image content, PixelContrast:25
- FOCUS: Hands off, Obs:, % look-around, Diopter range: ±2,
- Mag: 1±p5%, Cont: >95%, motion sensor 10° cone, Inter. Eye. adj: 52-72 mm Image Enhan & IFF: Weaponsight, motion sensor and computer interface The audio/video codec 200 in a portable access unit 100-100a or other client device is based around a single chip, standards-based codec that accepts analog or digital audio and video (i.e. NTSC or VGA) compresses this input, and multiplexes the compressed data with an external data stream. The preferred industry standards are: ITU H.263 based video, ITU G.722 based audio, and ITU H.221 based multiplexing. The audio video codec 200 in the portable access unit 100-100a can establish a link with a similar audio/video codec 200 associated with another portable access unit 100-100a or a remote media device 104, 125, 180 or 182. The signals from the codec 200 in the portable access unit 100a outputs the received and decompressed remote signals from the device for which the link was established. The interface between the codec 200 and communication device 202 as well as between the communication devices 202 of the general purpose node 150-150a and portable access unit 100-100a operate two-way with a high bandwidth suitable for transmitting video. Of this bandwith, the audio portion utilizes up to 64 kbps and the data from the sensor 104 utilizes the required amount for the type of sensor 104, with the remainder allocated to compressed video. The quality of the video at these data rates in excess of 128 kbps is at least equivalent to video teleconferencing quality video.

The audio/video codec 200 portion of the portable access unit 100-100a may further comprise video input and output ports, audio input and output ports, data input and output ports, and a the above-mentioned multimedia processor chip for packaging signals for data compression and decompression for transmission. Exemplary multimedia processors include the VCPEX chip by 8×8, Inc. of Santa Clara, Calif. or digital signal processing chips by Texas Instruments and others. The audio/video codec 200 further comprises a field processor gate array, electrically programmable read-only memory and random access memory for processing and packaging signals for compression and decompression The sensor 104 may comprise a commercially available pulse oximeter sensor or other type of bio-sensor. A pulse-oximeter sensor allows the measurement of pulse rate and oxygen saturation of the blood. Data from the sensor 104 is transmitted to the general purpose node 150-150a, and transmitted to any remote media device connected to any of the networks 170-172. The sensor 104 may comprise an "on body" wireless human performance and fatigue monitoring system that communicates with a belt-mounted transceiver/control module. The remote media device may comprise a processor 180-182 for display or logging of the real-time sensor signals.

The headset 102a comprises a heads-up display 120 comprising a transparent color LCD device for video signals received and processed by the codec 200. The headset 102a may further comprise, or have attached thereto, an integrated microphone 122 for receiving voice commands from the user of the portable access unit 100a or for communicating voice signals to a remote portable access unit 100 or remote media device. The headset may further comprise a speaker 124 or earpiece unit for presenting audio signals to the user. The portable access unit 100a may further comprise a digital camera 106 that may either be attached on the user's person, or to the headset 102a for providing video signals to other portable access units 100-100a or media devices.

Figure 3:
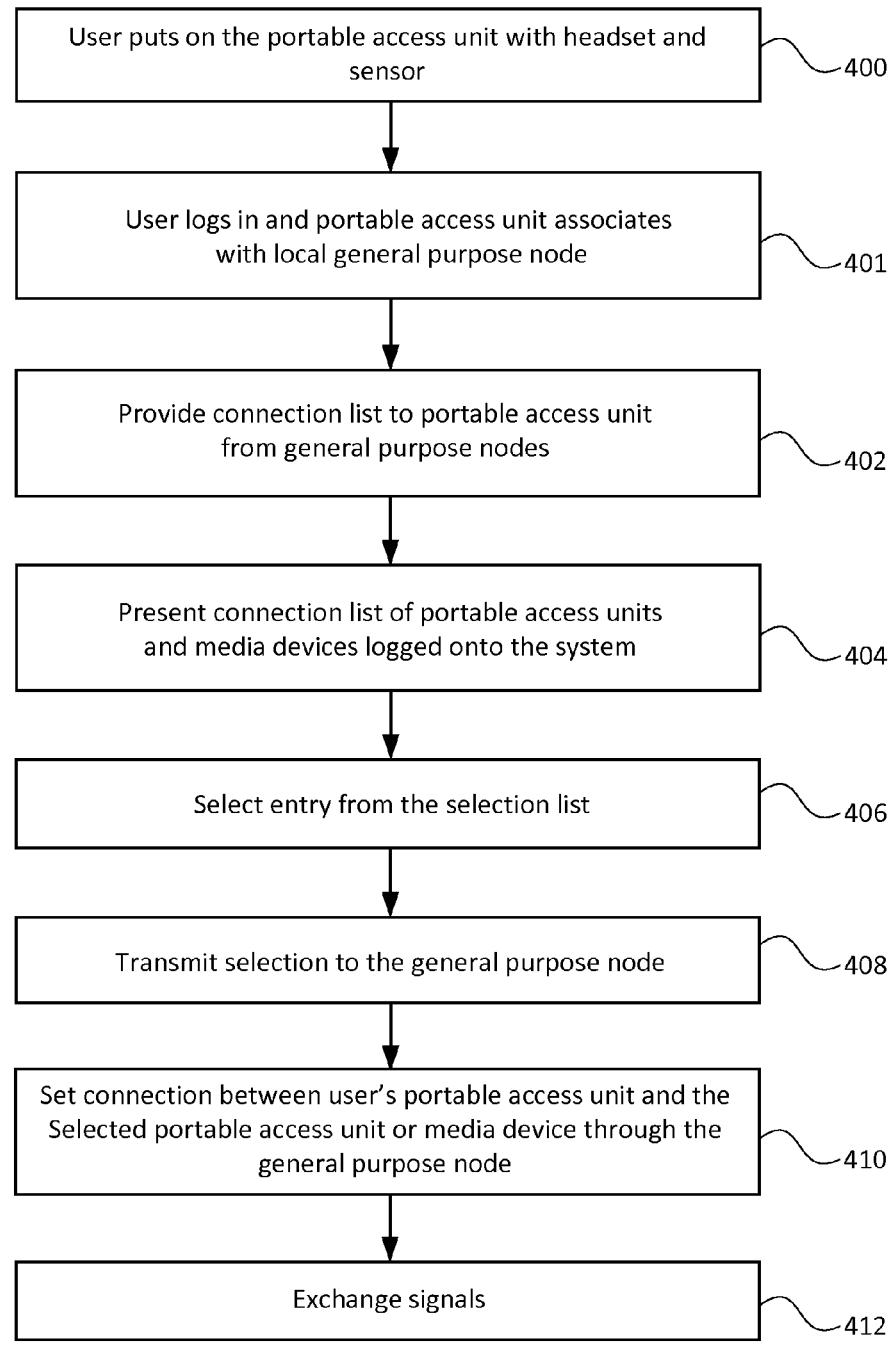
FIG. 3 is a flowchart illustrating a method performed using the system of FIG. 1.

With reference to FIG. 3, a flow diagram illustrating the method performed by the system of FIG. 1 is shown. A user puts on the headset 102a, portable access unit 100a, step 400. The user may log into the local general purpose node 150 wherein the portable access unit associates with the general purpose node 150 such that the user is added to a connection list stored in a random access memory device residing in the general purpose node 150, step 401. Data is provided from the general purpose node 150 to the portable access unit through the communication devices 202, step 402. The user is presented with a selection list 190 of portable access units 100-100a and media devices logged onto the system on the display 120, step 404. The user selects one of the entries from the selection list, step 406. The selection is transmitted to the general purpose node 150, step 408. The general purpose node 150 sets up a connection over the networks 170-174 for channeling data between the portable access unit 100a and the selected network device, step 410. The selected network device may comprise the processor 180 or other network client 182 for running a software application, a camera 125 for providing remote viewing operations to the user on the display 120, the Internet phone 104 for providing voice communications with the a remote user, or another portable access unit 100-100a over a remote general purpose node 150a. By providing control commands to the microphone 122 or other input system, such as a keyboard or handheld mouse, the user may conduct operations by transmitting commands between the portable access unit 100a and the general purpose node 150 which routs the control commands to the device that the user selected, step 412.

It will thus be seen that changes may be made in carrying out the above system and method and in the construction set forth without departing from the spirit and scope of the invention, it is intended that any and all matter contained in the above description and shown in the accompanying drawings shall be interpreted as illustrative and not in a limiting sense.

What is claimed is:

1. A device for in-situ biological monitoring of a user, comprising:
    a portable access unit to wirelessly access a network through a general purpose node coupled in communication with the network, the general purpose node also coupled in communication with a remote processor device, the portable access unit being associated with the remote processor device;
    a personal biological sensor to generate real-time sensor signals associated with the user;
    a codec of the personal access unit coupled to the biological sensor to receive and encode the real-time sensor signals;
    a transceiver of the personal access unit, comprising a transmitter connected to the codec that transmits a data stream provided by the codec over the network to the remote processor device.

2. The device of claim 1, wherein the personal biological sensor comprises a pulse oximeter sensor to measure a pulse rate and an oxygen saturation associated with the user.

3. The device of claim 1, further comprising:
    a video input of the portable access unit configured to receive real-time video information;
    a video output of the portable access unit configured to provide real-time video output; and
    a display coupled to the codec of the portable access unit to receive the real-time sensor signals and display the real-time sensor signals.

4. The device of claim 3, wherein the display is a wearable display.

5. The device of claim 1, wherein the remote processor device displays or logs the real-time sensor signals.

6. The device of claim 1, wherein the portable access unit dynamically associates with the general purpose node from a plurality of general purpose nodes.

7. The device of claim 1, wherein the remote processing device comprises a second portable access unit.

8. A method for in-situ biological monitoring of a user, the method comprising:
- wirelessly accessing, with a portable access unit, a network through a general purpose node coupled in communication with the network, the general purpose node also coupled in communication with a remote processor device, the portable access unit being associated with the remote processor device;
- generating, with a personal biological sensor, real-time sensor signals associated with the user;
- receiving and encoding, with a codec of the personal access unit, the real-time sensor signals;
- transmitting, with a transceiver of the personal access unit, a data stream provided by the codec over the network to the remote processor device.

9. The method of claim 8, wherein the personal biological sensor comprises a pulse oximeter sensor to measure a pulse rate and an oxygen saturation associated with the user.

10. The method of claim 8, further comprising:
- receiving, with a video input of the portable access unit, real-time video information;
- providing, with a video output of the portable access unit, real-time video output; and
- receiving, with a display, the real-time sensor signals and display the real-time sensor signals.

11. The method of claim 10, wherein the display is a wearable display.

12. The method of claim 8, further comprising:
- displaying or logging, with the remote processor device, the real-time sensor signals.

13. The method of claim 8, further comprising:
- dynamically associates with the general purpose node from a plurality of general purpose nodes.

14. The method of claim 8, wherein the remote processing device comprises a second portable access unit.

* * * * *